(12) United States Patent
Rochman et al.

(10) Patent No.: US 9,517,238 B2
(45) Date of Patent: Dec. 13, 2016

(54) COMPOSITIONS AND METHODS FOR TREATING ALLERGIC INFLAMMATION THROUGH INHIBITION OF NTRK1

(71) Applicant: CHILDREN'S HOSPITAL MEDICAL CENTER, Cincinnati, OH (US)

(72) Inventors: Mark Rochman, Cincinnati, OH (US); Marc E. Rothenberg, Cincinnati, OH (US)

(73) Assignee: CHILDREN'S HOSPITAL MEDICAL CENTER, Cincinnati, OH (US)

(*) Notice: Subject to any disclaimer, the term of this patent is extended or adjusted under 35 U.S.C. 154(b) by 0 days.

(21) Appl. No.: 14/934,589

(22) Filed: Nov. 6, 2015

(65) Prior Publication Data

US 2016/0129012 A1    May 12, 2016

Related U.S. Application Data (60) Provisional application No. 62/076,719, filed on Nov. 7, 2014.

(51) Int. Cl.
| | | |
|---|---|---|
| A01N 43/00 | (2006.01) |
| A61K 31/553 | (2006.01) |
| A61K 31/4545 | (2006.01) |
| A61K 45/06 | (2006.01) |
| A61K 31/00 | (2006.01) |

(52) U.S. Cl.
    CPC ............. *A61K 31/553* (2013.01); *A61K 31/00* (2013.01); *A61K 31/4545* (2013.01); *A61K 45/06* (2013.01)

(58) Field of Classification Search
    CPC .................................................. A61K 31/553
    USPC ..................................................... 514/211.08
    See application file for complete search history.

(56) References Cited

U.S. PATENT DOCUMENTS

| | | |
|---|---|---|
| 8,030,003 B2 | 10/2011 | Rothenberg |
| 9,260,756 B2 | 2/2016 | Rothenberg et al. |
| 2009/0269774 A1 | 10/2009 | Rothenberg et al. |
| 2011/0195500 A1 | 8/2011 | Rothenberg |
| 2012/0283117 A1 | 11/2012 | Rothenberg |
| 2013/0324435 A1 | 12/2013 | Rothenberg et al. |
| 2014/0228315 A1 | 8/2014 | Rothenberg et al. |
| 2014/0286896 A1 | 9/2014 | Rothenberg et al. |
| 2015/0045334 A1 | 2/2015 | Rothenberg et al. |

FOREIGN PATENT DOCUMENTS

| | | |
|---|---|---|
| WO | WO-2006/083390 A2 | 8/2006 |
| WO | WO-2006/119343 A1 | 11/2006 |
| WO | WO-2012/094643 A2 | 7/2012 |
| WO | WO-2012/094643 A3 | 7/2012 |
| WO | WO-2012/174549 A2 | 12/2012 |
| WO | WO-2012/174549 A9 | 12/2012 |
| WO | WO-2012/177945 A2 | 12/2012 |
| WO | WO-2012/177945 A3 | 12/2012 |
| WO | WO-2012/178188 A2 | 12/2012 |
| WO | WO-2012/178188 A3 | 12/2012 |
| WO | WO-2013/126834 A1 | 8/2013 |
| WO | WO-2015/142739 A1 | 9/2015 |
| WO | WO-2016/023026 A1 | 2/2016 |

OTHER PUBLICATIONS

Prakash et al. Expert Rev. Resp. Med. 4(3), 395-411 (2010).*
Vaishnavi et al. Nat Med. Nov. 2013 ; 19(11): 1469-1472.*
Oyoshi Current Opinion in Pediatrics, 2015, 27(6), 741-747.*
Chen et al. Jiepoukexue Jinzhan (2007), 13(4), 388-391.*
Rochlitzer et al. Biochemical Society Transactions (2006), 34(4), 594-599.*
Nassenstein et al. J Allergy Clin Immunol 2006;118:597-605.*
Rochman et al. Immunology | vol. 8 No. 4 | Jul. 2015, 785-198.*
Abonia, J.P. & Rothenberg, M.E. Eosinophilic esophagitis: rapidly advancing insights. *Annu. Rev. Med.* 63, 421-434 (2012).
Andrews, S.W. "Allosteric Small Molecule Inhibitors of the NGF/TrkA Pathway a New Approach to Treating Inflammatory Pain," http://www.arraybiopharma.com/files/6313/9810/8021/PubAttachment587.pdf. 33 pages.
Barski, A. et al. Chromatin poises miRNA- and protein-coding genes for expression. *Genome Res.* 19, 1742-1751 (2009).
Blanchard, C. et al. IL-13 involvement in eosinophilic esophagitis: transcriptome analysis and reversibility with glucocorticoids. *J. Allergy Clin. Immunol.* 120, 1292-1300 (2007).
Bonini, S. et al. Circulating nerve growth factor levels are increased in humans with allergic diseases and asthma. *Proc. Natl. Mad. Sci. USA* 93, 10955-10960 (1996).
Brightling, C.E., Saha, S. & Hollins, F. Interleukin-13: prospects for new treatments. *Clio. Exp. Allergy* 40, 42-49 (2010).
Brodeur, G.M. et al. Expression of TrkA, TrkB and TrkC in human neuroblastomas. *J. Neurooncol.* 31, 49-55 (1997).
Cho, S.J. et a/. Role of early growth response-1 (Egr-1) in interleukin-13-induced inflammation and remodeling. *J. Biol. Chem.* 281, 8161-8168 (2006).
Dalal, R. & Djakiew, D. Molecular characterization of neurotrophin expression and the corresponding tropomyosin receptor kinases (trks) in epithelial and stromal cells of the human prostate. *Mol. Cell. Endocrinol.* 134, 15-22 (1997).
Descamps, S. et al. Expression of nerve growth factor receptors and their prognostic value in human breast cancer. *Cancer Res.* 61, 4337-4340 (2001).
Dohrman, D.P., West, J.R. & Pantazis, N.J. Ethanol reduces expression of the nerve growth factor receptor, but not nerve growth factor protein levels in the neonatal rat cerebellum. *Alcohol. Clin. Exp. Res.* 21, 882-893 (1997).
Festuccia, C. et al. (Jan. 2007). "Tyrosine kinase inhibitor CEP-701 blocks the NTRK1/NGF receptor and limits the invasive capability of prostate cancer cells in vitro," *Int J. Oncol* 30(1)193-200.

(Continued)

Primary Examiner — Nizal Chandrakumar
(74) Attorney, Agent, or Firm — Mintz Levin Cohn Ferris Glovsky and Popeo, P.C.; Muriel Liberto, Esq.

(57) ABSTRACT

The invention provides methods of treating allergic inflammatory conditions using an anti-neurotrophin tyrosine kinase receptor 1 (NTRK1)-based therapeutic agent, and related compositions and methods.

10 Claims, 6 Drawing Sheets

(56) References Cited

OTHER PUBLICATIONS

Freund-Michel, V. & Frossard, N. The nerve growth factor and its receptors in airway inflammatory diseases. *Pharmacol. Ther* 117, 52-76 (2008).

Frossard, N., Freund, V & Advenier, C. Nerve growth factor and its receptors in asthma and inflammation. *Eur. J. Pharmacol.* 500, 453-465 (2004).

Hahn, C., Islamian, A.P., Renz, H. & Nockher, W.A. Airway epithelial cells produce neurotrophins and promote the survival of eosinophils during allergic airway inflammation. *J. Allergy Clin. Immunol.* 117, 787-794 (2006).

Indo, Y. et al. Mutations in the TRKA/NGF receptor gene in patients with congenital insensitivity to pain with anhidrosis. *Nat. Genet.* 13, 485-488 (1996).

Indo, Y. Molecular basis of congenital insensitivity to pain with anhidrosis (CIPA): mutations and polymorphisms in TRKA (NTRK1) gene encoding the receptor tyrosine kinase for nerve growth factor. *Hum Mutat.* 18, 462-471 (2001).

Indo, Y. Nerve growth factor and the physiology of pain: lessons from congenital insensitivity to pain with anhidrosis. *Clin. Genet.* 82, 341-350 (2012).

Ip, W.K., Wong, C.K., Li, M.L., Li, P.W., Cheung, P.F. & Lam, C.W. Interleukin-31 induces cytokine and chemokine production from human bronchial epithelial cells through activation of mitogen-activated protein kinase signalling pathways: implications for the allergic response. *Immunology* 122, 532-541 (2007).

Kuperman, D., Schofield, B., Wills-Karp, M. & Grusby, M.J. Signal transducer and activator of transcription factor 6 (Stat6)—deficient mice are protected from antigen-induced airway hyperresponsiveness and mucus production. *J. Exp. Med.* 187, 939-948 (1998).

Kuperman, D.A. et al. Direct effects of interleukin-13 on epithelial cells cause airway hyperreactivity and mucus overproduction in asthma. *Nat. Med.* 8, 885-889 (2002).

Lee, J.H. et al. Interleukin-13 induces dramatically different transcriptional programs in three human airway cell types. *Am. J. Respir. Cell Mol. Biol.* 25, 474-485 (2001).

Lei, L. & Parada, L.F. Transcriptional regulation of Trk family neurotrophin receptors. *Cell. Mol. Life Sci.* 64, 522-532 (2007).

Levi-Montalcini, R. The nerve growth factor 35 years later. *Science* 237 (4819):1154-1162 (1987).

Lim, E.J., Lu, T.X., Blanchard, C. & Rothenberg, M.E. Epigenetic r egulation of the IL-13-induced human eotaxin-3 gene by CREB-binding protein-mediated histone 3 acetylation. *J. Biol. Chem.* 286, 1 31 93-1 3204 (2011).

Lim, E. & Rothenberg, M.E. Demethylation of the human eotaxin-3 gene promoter leads to the elevated expression of eotaxin-3. *J. Immunol.* 192, 466-474 (2014).

Lovinsky-Desir, S. & Miller, R.L. Epigenetics, asthma, and allergic diseases: a review of the latest advancements. *Curr. Allergy Asthma Rep.* 12, 211-220 (2012).

Lu, T.X. et al. MiR-375 is downregulated in epithelial cells after IL-13 stimulation and regulates an IL-13-induced epithelial transcriptome. *Mucosa! Immunol.* 5, 388-396 (2012).

Madhusudan, S. et al. Tyrosine kinase inhibitors and cancer therapy. *Recent Results Cancer Res.* 172:25-44 (2007).

Meyer, L.R. et a/. The UCSC Genome Browser database: extensions and updates 2013. *Nucleic Acids Res.* 41 (Database issue), D64-D69 (2013).

Milbrandt, J. A nerve growth factor-induced gene encodes a possible transcriptional regulatory factor. *Science* 238, 797-799 (1987).

Raap, U. & Braunstahl, G.J. The role of neurotrophins in the pathophy-siology of allergic rhinitis. *Curr. Opin. Allergy Clin. Immunol.* 10, 8-13 (2010).

Russ, B.E., Prier, J.E., Rao, S. & Turner, S.J. T cell immunity as a tool for studying epigenetic regulation of cellular differentiation. *Front. Genet.* 4, 218 (2013).

Sin, A.Z., Roche, E.M., Togias, A., Lichtenstein, L.M. & Schroeder, J.T. Nerve growth factor or IL-3 induces more IL-13 production from basophils of allergic subjects than from basophils of nonallergic subjects. *J. Allergy Clin. Immunol.* 108, 387-393 (2001).

Tezza, G., Mazzei, F. & Boner, A. Epigenetics of allergy. *Early Hum. Dev.* 89 (Suppl 1), S20-S21 (2013).

Vaishnavi, A. et al. (Nov. 2013, e-published Oct. 27, 2013). "Oncogenic and drug-sensitive NTRK1 rearrangements in lung cancer," *Nat Med* 19(11):1469-1472.

Zediak, V.P., Johnnidis, J.B., Wherry, E.J. & Berger, S.L. Cutting edge: persistently open chromatin at effector gene loci in resting memory CD8 + Tcells independent of transcriptional status. *J. Immunol.* 186, 2705-2709 (2011).

Zheng, T., Oh, M.H., Oh, S.Y., Schroeder, J.T., Glick, A.B. & Zhu, Z. Transgenic expression of interleukin-13 in the skin induces a pruritic dermatitis and skin remodeling. *J. Invest. Dermatol.* 129, 742-751 (2009).

* cited by examiner

COMPOSITIONS AND METHODS FOR TREATING ALLERGIC INFLAMMATION THROUGH INHIBITION OF NTRK1

CROSS-REFERENCE TO RELATED APPLICATION

This application claims the benefit of U.S. Provisional Patent Application No. 62/076,719, filed Nov. 7, 2014, the content of which is incorporated herein by reference in its entirety.

STATEMENT REGARDING FEDERALLY-SPONSORED RESEARCH

This invention was made with government support under A1083450, A1045898, and DK078392 awarded by the National Institutes of Health. The government has certain rights in the invention.

FIELD OF THE INVENTION

The invention disclosed herein generally relates to compositions and methods for treating allergic inflammation.

BACKGROUND

Interleukin 13 (IL-13)-mediated allergic inflammation is a hallmark of a number of diseases including asthma, atopic dermatitis, and eosinophilic esophagitis (EoE). IL-13 induces robust, cell-specific changes in gene expression and a majority of IL-13-mediated transcriptional and pathological changes are signal transducer and activator of transcription 6 (STAT6) dependent. For example, in a murine model of EoE induced by IL-13 delivery into the lungs, eosinophilic infiltration and epithelial hyperplasia in the esophagus occur in a STAT6-dependent manner. Likewise, in human intestinal, airway, and esophageal epithelial cells, induction of the eosinophil-specific chemokine (C-C Motif) ligand 26 (CCL26 also referred to as eotaxin-3) by IL-13 requires STAT6 expression. To date, nearly all targets of IL-13 have been signaling molecules and/or soluble mediators of inflammation.

NGF was originally described as a critical factor for the survival and maintenance of sympathetic and sensory neurons, yet NGF is also considered a biomarker of asthmatic inflammation, with increased levels correlating with the severity of the disease. Early growth response protein 1 (EGR1), a central transcriptional target of NGF, has a key role in IL-13-induced inflammation, fibrosis, alveolar remodeling and cytokine response. Neurotrophin tyrosine kinase receptor 1 (NTRK1) is a high affinity receptor for NGF. However, a connection between NTRK1 and these EGR1-associated inflammatory and/or remodeling pathways has not been established.

Asthma is a common chronic inflammatory disease of the airways thought to be caused by a combination of genetic and environmental factors. It is clinically classified according to the frequency of symptoms, forced expiratory volume in one second (FEV1), and peak expiratory flow rate. Treatment options include inhaled short-acting beta-2 agonists, e.g., salbutamol, for acute symptoms, and oral or inhaled corticosteroids.

Atopic dermatitis, also called atopic eczema, is a type of inflammation of the skin. The cause is not known but believed to involve genetics, immune system dysfunction, environmental exposures, and skin permeability problems. Atopic dermatitis affects about 20% of people at some point in their lives and is more common in younger children.

Eosinophilic esophagitis (EoE) is considered to be a chronic immune system disease. Although it was identified only during the last twenty years, it is now considered a major cause of digestive system (gastrointestinal) illness. In EoE, eosinophils (a type of white blood cell) build up in the lining of the esophagus. This buildup, which may be a reaction to foods, allergens or acid reflux, can inflame and/or injure the esophageal tissue. Damaged esophageal tissue can lead to difficulty swallowing or lead to other complications. Symptoms include difficulty swallowing (dysphagia), food impaction, chest pain that is often centrally located and does not respond to antacids, persistent heartburn, upper abdominal pain, lack of response to gastroesophageal reflux disease (GERD) medication, and backflow of undigested food (regurgitation).

Current clinical standards for diagnosis of EoE include (i) endoscopy to inspect the lining of the esophagus for inflammation and swelling, horizontal rings, vertical furrows, narrowing (strictures) and white spots; (ii) biopsy of esophageal tissue with one biopsy showing more than 15 eosinophils per high power field in patients using a proton pump inhibitor (PPI) for approximately 8 weeks.

Treatment for EoE that is not responsive to PPIs includes an orally administered topical steroid, such as fluticasone or budesonide. Where topical steroids prove ineffective, prednisone may be prescribed

SUMMARY OF THE INVENTION

The present disclosure provides methods of treating an allergic inflammatory disease, disorder, or condition in a subject in need thereof. The methods comprise administering to the subject an amount of an anti-neurotrophin tyrosine kinase receptor 1 (NTRK1)-based therapeutic agent. The anti-NTRK1-based therapeutic agent is administered in an amount effective to suppress NTRK1 activity in cells of the subject, thereby treating the allergic inflammatory condition in the subject. In embodiments, the cells are epithelial cells. In embodiments, the cells are cells of a target tissue in the subject. In embodiments, the target tissue is skin, nasal, tracheal, lung, or esophageal tissue.

In embodiments, the anti-NTRK1-based therapeutic agent is effective to suppress NTRK1 activity in the cells of the subject, relative to untreated cells. In embodiments, the anti-NTRK1-based therapeutic agent is effective to suppress NTRK1 gene expression or protein expression, or both. In embodiments, the amount of the anti-NTRK1-based therapeutic agent is effective to ameliorate one or more symptoms of the allergic inflammatory disease, disorder, or condition.

In embodiments, the anti-NTRK1-based therapeutic agent is a tyrosine kinase inhibitor, an NTRK1-Fc fusion protein, an NTRK1 anti-sense polynucleotide, an NTRK1-directed miRNA, an NTRK1-directed shRNA, or an NTRK1-directed antibody. In embodiments, the anti-NTRK1-based therapeutic agent is a tyrosine kinase inhibitor. In embodiments, the tyrosine kinase inhibitor is lestaurtinib (CEP-701) or crizotinib. In embodiments, the anti-NTRK1-based therapeutic agent is selected from AR-786, AR-256, and AR-618.

In embodiments, the allergic inflammatory condition is characterized by an interleukin 13 (IL-13) mediated allergic inflammation. In embodiments, the allergic inflammatory condition is selected from asthma, atopic dermatitis, allergic rhinitis, and eosinophilic esophagitis (EoE).

In embodiments, the method further comprises administering to the subject at least one additional active agent. In embodiments, the at least one additional active agent is an anti-inflammatory agent. In embodiments, the at least one additional active agent is an IL-13 inhibitor, a non-steroidal anti-inflammatory drug (NSAID), a cytokine inhibitor, or a steroid.

The disclosure also provides methods of treating eosinophilic esophagitis (EoE) in a subject in need thereof, comprising administering to the subject an amount of an anti-neurotrophin tyrosine kinase receptor 1 (NTRK1)-based therapeutic agent effective to suppress NTRK1 activity in the subject, thereby treating the EoE in the subject. In embodiments, the NTRK1-based therapeutic agent is a tyrosine kinase inhibitor, an NTRK1-Fc fusion protein, an NTRK1 anti-sense polynucleotide, an NTRK1-directed miRNA, an NTRK1-directed shRNA, or an NTRK1-directed antibody. In embodiments, the NTRK1-based therapeutic agent is selected from lestaurtinib (CEP-701), crizotinib, AR-786, AR-256, and AR-618.

The disclosure also provides methods of suppressing NTRK1 activity in a cell, the method comprising contacting the cell with an anti-NTRK1 agent in an amount effective to suppress NTRK1 expression in the cell.

BRIEF DESCRIPTION OF THE DRAWINGS

FIG. 2. Effect of IL-13 stimulation and STAT6 silencing on epigenetic status of NTRK1. In A, levels of H3K9Ac, H3K27Ac, and H3K4me3 in the promoters of CCL26, NTRK1, and MYOD after IL-13 stimulation were quantified by ChIP-RT-PCR. Data from 3 independent experiments calculated as percentage of signal in input DNA normalized to the level of signal in PPIA gene are presented as mean values with standard error measurements. In B, levels of histone modification in the NTRK1 promoter following induction with IL-13 for 24 hr were quantified by RT-PCR in control (Ctrl) and TE-7 cells where the STAT6 gene was silenced by shRNA (STAT6KD). Combined data for 2 independent experiments are shown. *$p<0.05$, $p<0.01$, *$p<0.001$, ****$p<0.0001$, ns, not significant.

FIG. 3. NTRK1 confers epithelial cell responsiveness to NGF. In A, shown is a Western blot analysis of primary esophageal epithelial cells pre-treated with IL-13 for 24 hr and then treated with recombinant human NGF for 0, 5, or 15 min pNTRK1 indicates phosphorylated protein (arrow). In B, shown is Western blot analysis of TE-7 cells pre-treated with IL-13 for 24 hr and then treated with NGF for 5 min pNTRK1 and pERK1/2 indicate phosphorylated proteins, arrow points at pNTRK1. In C, the kinetics of NTRK1 phosphorylation were assessed by Western blot. Cells were pre-treated with IL-13 for 24 hr and then treated with NGF for 5, 15 or 30 min. For A-C, phosphorylation was assessed at tyrosine residues Tyr674/675 in the catalytic domain of NTRK1. In D, kinetic analysis of EGR1 and EGR3 mRNA in TE-7 cells pre-treated with IL-13 for 24 hr followed by treatment with NGF for 1, 2, or 6 hrs was performed by RT-PCR. Fold change indicates increase over untreated (no IL-13) cells stimulated with NGF (+NGF). NGF was used at the concentration of 100 ng/ml. Data for 3 independent experiments are presented as mean value with standard error measurements; ****$p<0.0001$, *$p<0.05$. In E, EGR1 and EGR3 protein levels in TE-7 cells pre-treated with IL-13 for 24 hr followed by treatment with NGF were analyzed by Western blot; p38 serves as a loading control.

FIG. 4. NTRK1, NGF, and EGR1 expression in human allergic inflammation. In A, RT-PCR analysis of NTRK1 in biopsies was performed in unaffected control patients (Ctrl, n=13), patients with active EoE (EoE, n=12), and EoE patients who responded to swallowed steroid treatment (fluticasone responders [FPR], n=13); ***$p<0.001$; ns, not significant. In B and C, the graphs show Pearson correlation of NTRK1 expression with IL-13 levels and peak eosinophil counts in EoE biopsies. In D, a representative Western blot shows expression of NTRK1 in a control and EoE biopsy; p38 serves as a loading control. In E, quantification of NTRK1 in control and active EoE biopsies is shown (n=5 each); *$p<0.05$. Expression level was normalized to the level of GAPDH. In F, RT-PCR analysis of NGF and CCL26 was performed in control and EoE biopsies (n=10 each); ****$p<0.0001$; ns, not significant. In G, amount of NGF and CCL26 protein was measured by ELISA in control and active EoE biopsies (n=5 each); *$p<0.05$; ns, not significant. In H, immunohistochemistry for NTRK1 and NGF in control (Ctrl, no eosinophils present in biopsy) and representative active EoE biopsy (EoE, 199 eosinophils per high-power field [HPF]) is shown. The bar is 20 □m for X20 images (top 6 panels) and 50 □m for X40 images (bottom 2 panels). A total of 9 control and 10 active EoE biopsies were stained. In I, EGR1 mRNA was measured by RT-PCR in esophageal biopsies of unaffected control (Ctrl) patients and patients with active EoE (n=10 each). ***$p<0.001$. In J, shown is a representative Western blot of EGR1 and NTRK1 in control and active EoE biopsies. GAPDH serves as a loading control. In K, relative level of EGR1 expression in biopsies is shown (n=5 each); *$p<0.05$. Expression level was normalized to the level of p38 protein. For A, F and I, mean values of gene expression were normalized to the level of GAPDH. For A, E, F, G, I and K, data are presented as box and whiskers plot.

FIG. 5. IL-13 and NGF/NTRK1 synergistically stimulate CCL26 production. In A-D, transcriptional levels of CCL26, SERPINB4, KITLG and ID3 after IL-13 and/or NGF stimulation of TE-7 cells stably expressing NTRK1 were measured by RT-PCR. Induction was performed for 6 hr, IL-13 concentration was 1 ng/ml, NGF was used at 100 ng/ml. Expression was normalized to the level of GAPDH. In E, CCL26 protein level in cell supernatant was measured by ELISA. Cells were stimulated with IL-13 and NGF (100 ng/ml) for 24 hr; mean fold induction relative to untreated cells is shown. Error bars represent standard error of the mean for 4 independent experiments. In F, shown is the relative level of expression of the indicated genes following down regulation of EGR1 by siRNA in TE-7 cells. Expression of genes in cells transfected with control siRNA was set as 1 (dotted line). Data for 4 to 5 independent experiments are presented as box and whiskers plot; **$p<0.0001$, *$p<0.001$, **$p<0.01$, ns, not significant.

FIG. 6. Model for propagation of IL-13-mediated allergic inflammation in epithelial cells. Prior to IL-13 stimulation (represented by unaffected cell), promoters of CCL26 and NTRK1 are epigenetically poised for activation (small light purple circles with broken lines), but genes are either not transcribed (NTRK1) or transcribed at a low level (CCL26, broken arrow). Early response gene EGR1 is transcribed at a detectable level (represented by solid arrow). NGF is present in the environment but does not elicit a transcriptional response. During allergic inflammation (exemplified by active EoE), IL-13 initially induces epigenetic and transcriptional responses of its targets, as shown for CCL26 and NTRK1 (large purple circles with solid lines and green arrows) and increased expression of NTRK1. Subsequently, NGF binds to NTRK1 and elicits signal transduction (illustrated by phosphorylation of NTRK1 on kinase domain [yellow ovals]), which leads to an NGF/NTRK1-mediated transcriptional response (e.g. induction of EGR1, blue arrow), as well as a synergistic effect on transcription of key inflammatory genes (orange arrows, exemplified by CCL26). IL-13R, IL-13 receptor; NUC, nucleus; CYT, cytoplasm.

DETAILED DESCRIPTION OF THE INVENTION

The present disclosure provides methods for treating an allergic inflammatory condition in a subject by suppressing anti-neurotrophin tyrosine kinase receptor 1 (NTRK1) activity, and related methods. The methods comprise administering an anti-NTRK1-based therapeutic agent to a subject in need of treatment for an allergic inflammatory condition. The methods described here are based, in part, on the identification of NTRK1 as a direct transcriptional and epigenetic target of IL-13 with a contributory role in allergic inflammation, and further the identification of this receptor, but not its ligand, as the limiting checkpoint in the pathway. The additional finding that NTRK1 is highly increased in human esophageal biopsies from eosinophilic esophagitis (EoE) patients and synergizes with IL-13 in propagating allergic inflammation provides the rationale for pharmacological targeting of NTRK1 signaling for the treatment of allergic inflammatory conditions.

In embodiments, an anti-NTRK1-based therapeutic agent includes at least one of a compound or composition that suppresses NTRK1 activity. In some embodiments, the compound or composition that suppresses NTRK1 activity includes a tyrosine kinase inhibitor, an NTRK1-Fc fusion protein, an NTRK1 anti-sense polynucleotide, an NTRK1-directed miRNA, an NTRK1-directed shRNA, or an NTRK1-directed antibody, including a humanized antibody. In embodiments, the compound is a small organic molecule such as AR-786, AR-256, and AR-618. In embodiments, the compound is a tyrosine kinase inhibitor, for example, lestaurtinib (CEP-701) or crizotinib. In embodiments, NTRK1 activity is suppressed by inhibiting NTRK1 gene expression, inhibiting NTRK1 protein expression, or inhibiting NTRK1 kinase activity, or any combination thereof. For example NTRK1 kinase activity may be inhibited directly, by an agent that inhibits the kinase function of the NTRK1 protein, or indirectly, for example, by inhibiting NTRK1 gene or protein expression, thereby reducing the amount of NTRK1 protein in the cell and thereby indirectly inhibiting NTRK1 kinase activity in the cell.

Methods of Treatment

The present disclosure provides methods for the treatment of an allergic inflammatory condition in a subject in need thereof by administering to the subject an effective amount of an anti-NTRK1-based therapeutic agent. In embodiments, the effective amount is a therapeutically effective amount. In embodiments, the effective amount is the amount effective to ameliorate one or more symptoms of the allergic inflammatory condition. In embodiments, the effective amount is the amount effective to suppress NTRK1 activity in cells of the subject. In embodiments, the cells are cells of a target tissue affected by an allergic inflammatory condition. In embodiments, the tissue is skin tissue, esophageal tissue, nasal tissue, tracheal tissue, or lung tissue, such as tissue of the bronchi or bronchioles. In embodiments, NTRK1 activity is suppressed by inhibiting NTRK1 gene expression, inhibiting NTRK1 protein expression, or inhibiting NTRK1 kinase activity, or any combination thereof. For example, inhibiting NTRK1 gene expression may also inhibit NTRK1 protein expression and NTRK1 kinase activity.

In embodiments, the allergic inflammatory condition is characterized by an interleukin 13 (IL-13) mediated allergic inflammation. In embodiments, the allergic inflammatory condition is asthma, atopic dermatitis, allergic rhinitis, or eosinophilic esophagitis (EoE).

The present disclosure also provides methods comprising combination therapy for the treatment of allergic inflammatory condition. As used herein, "combination therapy" or "co-therapy" includes the administration of an effective amount of an anti-NTRK1-based therapeutic agent as part of a specific treatment regimen intended to provide the beneficial effect from the co-action of the anti-NTRK1-based therapeutic agent and an additional active agent, e.g., an additional active pharmaceutical ingredient (API). The beneficial effect of the combination includes, but is not limited to, pharmacokinetic or pharmacodynamic co-action resulting from the combination of therapeutic compounds. The beneficial effect of the combination may also relate to the mitigation of a toxicity, side effect, or adverse event associated with another agent in the combination. "Combination therapy" is not intended to encompass the administration of two or more of these therapeutic compounds as part of separate monotherapy regimens that incidentally and arbitrarily result in a beneficial effect that was not intended or predicted.

The at least one additional active agent may be a therapeutic agent, for example an anti-inflammatory agent, or a non-therapeutic agent, and combinations thereof. With respect to therapeutic agents, the beneficial effect of the combination includes, but is not limited to, pharmacokinetic or pharmacodynamic co-action resulting from the combination of therapeutically active compounds. With respect to nontherapeutic agents, the beneficial effect of the combination may relate to the mitigation of a toxicity, side effect, or adverse event associated with a therapeutically active agent in the combination.

In embodiments, the at least one additional active agent is an anti-inflammatory agent selected from an IL-13 inhibitor, a non-steroidal anti-inflammatory drug (NSAID), a steroid, and a cytokine inhibitor.

In one embodiment, the at least one additional agent is a non-therapeutic agent which mitigates one or more side effects of the anti-NTRK1-based therapeutic agent in the composition, or which mitigates one or more side effects of the at least one additional active agent in the composition.

In the context of combination therapy, the administration of the anti-NTRK1-based therapeutic agent, may be simultaneous with or sequential to the administration of the one or more additional active agents. In another embodiment, administration of the different components of a combination therapy may be at different frequencies. The one or more additional agents may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a compound of the present disclosure.

The one or more additional active agents can be formulated for co-administration with the anti-NTRK1-based therapeutic agent in a single dosage form. The one or more additional active agents can be administered separately from the dosage form that comprises the anti-NTRK1-based therapeutic agent. When the additional active agent is administered separately from the anti-NTRK1-based therapeutic agent, it can be by the same or a different route of administration as the anti-NTRK1-based therapeutic agent.

Preferably, the administration of a composition comprising the anti-NTRK1-based therapeutic agent in combination with one or more additional active agents provides a synergistic response in the subject being treated. In this context, the term "synergistic" refers to the efficacy of the combination being more effective than the additive effects of either single therapy alone. The synergistic effect of a combination therapy according to the disclosure can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

"Combination therapy" also embraces the administration of the compounds of the present disclosure in further combination with non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

In embodiments, the amount of the anti-NTRK1-based therapeutic agent administered to the subject is a therapeutically effective amount. The term "therapeutically effective amount" refers to an amount sufficient to treat, ameliorate a symptom of, reduce the severity of, or reduce the duration of the disease or disorder being treated or enhance or improve the therapeutic effect of another therapy, or sufficient to exhibit a detectable therapeutic effect in the subject. In one embodiment, the therapeutically effective amount of the anti-NTRK1-based therapeutic agent is the amount effective to inhibit NTKR1 kinase activity.

An effective amount of the anti-NTRK1-based therapeutic agent can be administered once or twice daily, from two to five times daily, up to two times or up to three times daily, or up to eight times daily.

In accordance with the methods described herein, a "subject in need thereof" is a subject having an allergic inflammatory disease, disorder, or condition, or a subject having an increased risk of developing an allergic inflammatory disease, disorder, or condition relative to the population at large. The subject in need thereof can be one that is "non-responsive" or "refractory" to a currently available therapy. In this context, the terms "non-responsive" and "refractory" refer to the subject's response to therapy as not clinically adequate to relieve one or more symptoms associated with the allergic inflammatory disease, disorder, or condition. In one aspect of the methods described here, the subject in need thereof is a subject having an allergic inflammatory disease, disorder, or condition that is refractory to standard therapy.

A "subject" includes a mammal. The mammal can be any mammal, for example, a human, primate, vertebrate, bird, mouse, rat, fowl, dog, cat, cow, horse, goat, camel, sheep or a pig. Preferably, the mammal is a human. The term "patient" refers to a human subject.

The present disclosure also provides a monotherapy for the treatment of allergic inflammatory disease, disorder, or condition as described herein. As used herein, "monotherapy" refers to the administration of a single active or therapeutic compound, e.g., an anti-NTRK1-based therapeutic agent, to a subject in need thereof.

As used herein, "treatment", "treating" or "treat" describes the management and care of a patient for the purpose of combating a disease, condition, or disorder and includes the administration of an anti-NTRK1-based therapeutic agent to alleviate the symptoms or complications of the allergic inflammatory disease, disorder, or condition.

As used herein, "prevention", "preventing" or "prevent" describes reducing or eliminating the onset of the symptoms or complications of the allergic inflammatory disease, disorder, or condition and includes the administration of an anti-NTRK1-based therapeutic agent to reduce the onset, development or recurrence of symptoms of the disease, disorder, or condition.

In one embodiment, the administration of an anti-NTRK1-based therapeutic agent leads to the elimination of a symptom or complication of the allergic inflammatory disease, disorder, or condition being treated, however elimination of the disease, disorder, or condition is not required. In one embodiment, the severity of the symptom is decreased.

Pharmaceutical Compositions and Formulations

The present disclosure provides pharmaceutical compositions comprising an amount of an anti-NTRK1-based therapeutic agent.

In one embodiment, the an anti-NTRK1-based therapeutic agent is combined with at least one additional active agent in a single dosage form. In embodiments, the at least one additional active agent is selected from an anti-inflammatory agent selected from an IL-13 inhibitor, a non-steroidal anti-inflammatory drug (NSAID), a steroid, and a cytokine inhibitor, and combinations thereof.

A "pharmaceutical composition" is a formulation containing an anti-NTRK1-based therapeutic agent in a pharmaceutically acceptable form suitable for administration to a subject. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient subject or patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in m2, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

For example, the dosage unit form can comprise 1 nanogram to 2 milligrams, or 0.1 milligrams to 2 grams; or from 10 milligrams to 1 gram, or from 50 milligrams to 500 milligrams or from 1 microgram to 20 milligrams; or from 1 microgram to 10 milligrams; or from 0.1 milligrams to 2 milligrams.

The pharmaceutical compositions can take any suitable form (e.g., liquids, aerosols, solutions, inhalants, mists, sprays; or solids, powders, ointments, pastes, creams, lotions, gels, patches and the like) for administration by any desired route (e.g, pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the disclosure may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present disclosure with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present disclosure may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present disclosure together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present disclosure may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present disclosure as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present disclosure can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the disclosure are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present disclosure also provides packaging and kits comprising pharmaceutical compositions for use in the methods of the present disclosure. The kit can comprise one or more containers selected from the group consisting of a bottle, a vial, an ampoule, a blister pack, and a syringe. The kit can further include one or more of instructions for use in treating and/or preventing a disease, condition or disorder of the present disclosure, one or more syringes, one or more applicators, or a sterile solution suitable for reconstituting a pharmaceutical composition of the present disclosure.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

EXAMPLES

The following non-limiting examples are provided to further illustrate embodiments of the invention disclosed herein. It will be appreciated by those of skill in the art that the techniques disclosed in the examples that follow represent approaches that have been found to function well in the practice of the invention and thus can be considered to constitute examples of modes for its practice. However, those of skill in the art will, in light of the present disclosure, appreciate that many changes can be made in the specific embodiments that are disclosed and still obtain a like or similar result without departing from the spirit and scope of the invention.

SUMMARY

We herein employed RNA-sequencing analysis of the IL-13-mediated transcriptional response in the human esophageal epithelial cell line TE-7. We identified a set of 24 early IL-13 target genes, which included NTRK1. In response to IL-13, NTRK1 was dramatically induced in epithelial cells and the NTRK1 promoter showed rapid accumulation of multiple activating epigenetic marks; both transcriptional and epigenetic changes occurred in a STAT6-dependent manner Notably, NTRK1 was the only receptor tyrosine kinase (RTK) with these characteristics. Functional analysis showed that IL-13-induced NTRK1 responded to NGF by activating EGR1 signaling and synergistically inducing a number of IL-13 target genes including CCL26, Serpin Peptidase Inhibitor, Clade B, Member 4 (SERPINB4) and KIT Ligand (KITLG). EGR1 induction was significantly diminished by gene silencing or by pharmacological inhibition of NTRK1. Translational studies showed elevated expression of NTRK1 in allergic tissue from patients with eosinophilic esophagitis (EoE). In summary, we have identified NTRK1 as a direct transcriptional and epigenetic target of IL-13 with a contributory role in allergic inflammation.

Transcriptional Signature of IL-13 Response in TE-7 Esophageal Epithelial Cells

To gain insight into the transcriptional signature of IL-13-mediated allergic inflammation, we analyzed the kinetics of the transcriptional response to IL-13 in the human esophageal epithelial cell line TE-7 17. Cells were stimulated with IL-13 for 2, 6, and 24 hr and subjected to RNA-sequencing analysis. By applying differential expression analysis for sequence count data (DESeq), we identified 767 unique genes significantly affected by IL-13 during the course of stimulation ($p<0.05$); 24, 328, and 573 genes were affected after 2, 6, and 24 hr of stimulation, respectively. Comparing the transcriptional response in TE-7 cells with the transcriptome of diseased tissue (esophageal biopsies from patients with active EoE) and of IL-13-induced primary esophageal epithelial cells revealed a remarkable similarity in the regulation of overlapping genes, including induction of the EoE hallmark genes CCL26 and cadherin 26 (CDH26). Kinetic analysis of the IL-13-mediated transcriptome of TE-7 cells revealed dynamic changes in gene expression, with early response genes mostly affected after 2 hr of stimulation and late response genes significantly changed only after 24 hr of IL-13 stimulation.

Of the 24 early target genes that responded to IL-13 within 2 hr of stimulation, 20 genes were significantly altered at 6 hr and 24 hr. Of these 20 genes, only inhibitor of DNA binding 3 (ID3) was decreased after 24 hr, whereas other genes were significantly up regulated at all assessed time points. In agreement with previous findings, CCL26 was one of the early transcriptional targets of IL-13. Among early target genes, we found known inhibitors of cytokine signaling, suppressor of cytokine signaling 1 (SOCS1) and cytokine inducible SH2-containing protein (CISH), which can provide a negative feedback loop for cytokine signaling. We also detected genes such as hyaluronan synthase 3 (HAS3), heparan sulfate (glucosamine) 3-O-sulfotransferase 1 (HS3ST1), and glucosaminyl (N-acetyl) transferase 3, mucin type (GCNT3), which are involved in the synthesis of unbranched glycosaminoglycan hyaluronan, heparan sulfate, and mucin, major constituents of the epithelial extracellular environment. These genes have been previously identified in EoE biopsies and in primary human esophageal epithelial cells induced with IL-13. Notably, among early responsive genes, there was a member of the AT-rich interaction domain family of DNA-binding proteins, AT-rich interactive domain 5B (ARIDSB), which functions as a cofactor in a histone demethylation process, and mitogen-activated protein kinase kinase kinase (MAP3K14), a NF-kB-inducing kinase that participates in regulating tumor necrosis factor (TNF) and interleukin 1 (IL-1) receptor signaling, suggesting that initial stimulation by IL-13 can affect subsequent stimuli by modulating chromatin structure and signaling events. A member of the epithelial-specific ETS transcription factors ETS homologous factor (EHF), a RUNX family protein runt-related transcription factor 2 (RUNX2), and the zinc finger protein B-cell CLL/lymphoma 11B (BCL11B) were also identified as early targets of IL-13 in TE-7 cells. These transcription factors have been previously implicated in regulating epithelial cell proliferation and differentiation. Interleukin 31 (IL-31), which is normally produced by activated T cells 30, was highly induced in TE-7 epithelial cells. Interestingly, epithelial cells have been shown to respond synergistically to IL-13 and IL-31 by secreting inflammatory cytokines, such as epidermal growth factor (EGF), vascular endothelial growth factor (VEGF), and chemokine (C-C motif) ligand 2 (CCL2), suggesting a positive feedback loop in inducing allergic inflammation.

We identified NTRK1 as one of the most highly IL-13-induced genes in TE-7 cells. NTRK1 is highly expressed in the nervous system and has a role in the survival of neurons, as well as in sensitivity to pain. A growing body of evidence links the NGF/NTRK1 pathway to the pathogenesis of allergic inflammation, such as asthma and allergic rhinitis, yet a direct link between IL-13- and NGF-mediated pathways has not been shown.

NTRK1 is a Unique RTK Transcriptionally Induced by IL-13

Figure 1:
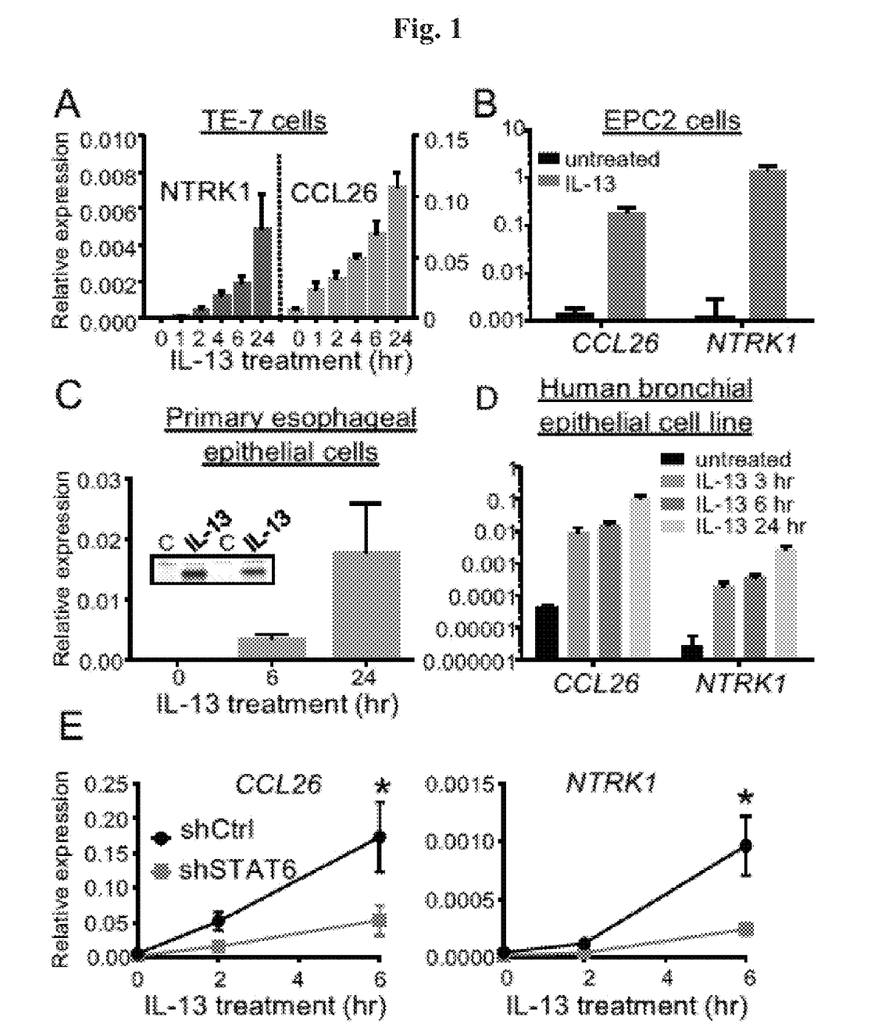
FIG. 1. IL-13-stimulated NTRK1 induction in epithelial cells and effect of STAT6 gene silencing. In A-D, shown is quantitative RT-PCR analysis of NTRK1 and CCL26 transcription in TE-7 cells, EPC2 epithelial cell ALI culture, primary esophageal epithelial cells, and human bronchial epithelial cells. Cells were treated with IL-13 at 100 ng/ml for the indicated periods of time or for 6 days for EPC2 cells. The inset in C shows Western blot for NTRK1 in two independent cultures of primary esophageal epithelial cells stimulated with IL-13. In E, the effect of STAT6 gene silencing by shRNA on NTRK1 and CCL26 induction in TE-7 cells was quantified by RT-PCR. TE-7 cells were stimulated with IL-13 (1 ng/ml) for the indicated periods of time. shCtrl, control shRNA; shSTAT6, shRNA against STAT6. Data for 3 to 4 independent experiments are presented as mean values for gene expression normalized to the level of GAPDH with standard error measurements.

In light of the emerging role of NGF/NTRK1 signaling in the pathogenesis of allergic inflammation, we were intrigued by the robust induction of NTRK1 by IL-13 in TE-7 cells. We hypothesized that the NGF/NTRK1 and IL-13/STAT6 pathways cooperate in propagating allergic inflammation. We therefore focused on exploring the mechanism of IL-13-mediated NTRK1 induction in epithelial cells and the functional outcome of this induction. First, we validated our RNA-sequencing finding by testing the kinetics of NTRK1 expression in TE-7 cells by real-time polymerase chain reaction (RT-PCR). In agreement with RNA-sequencing data, this analysis revealed that the NTRK1 transcript was detectable as early as 2 hr after stimulation and progressively increased at the assessed time points over a 24-hr period mirroring induction of CCL26 (FIG. 1A). We further assessed expression of NTRK1 in the esophageal epithelial cell line EPC2 grown at air-liquid interface (ALI), primary epithelial cells obtained from esophageal biopsies, and human bronchial epithelial cells after stimulation with IL-13. The results demonstrated that NTRK1 was highly induced by IL-13 in epithelial cells of different origin; the kinetics of NTRK1 induction paralleled those of CCL26 (FIG. 1B-D). Finally, we tested whether induction of NTRK1 was dependent on IL-13 signaling. By stably integrating shRNA against STAT6 in TE-7 cells, we decreased levels of STAT6 mRNA and protein to 20-30% of that of control cells. By stimulating these cells with IL-13, we found that transcriptional induction of both CCL26 and NTRK1 was significantly decreased, indicating STAT6 dependency (FIG. 1E).

As approximately 90 RTKs have been identified in the human genome, we investigated how many of these molecules besides NTRK1 were altered in the course of IL-13 induction. From RNA-sequencing data, we identified 29 RTKs that were expressed in either untreated or IL-13-stimulated TE-7 cells (reads per kilobase per million mapped reads [RPKM]>1) and analyzed the effect of IL-13 on their transcription. We found that transcription of 6 members of the RTK family was significantly affected by IL-13 in at least one time point of stimulation (p<0.05); however, NTRK1 was unique in that it was the only RTK strongly and consistently up regulated throughout IL-13 stimulation.

IL-13 Epigenetically Regulates NTRK1 in a STAT6-Dependent Manner

Figure 2:
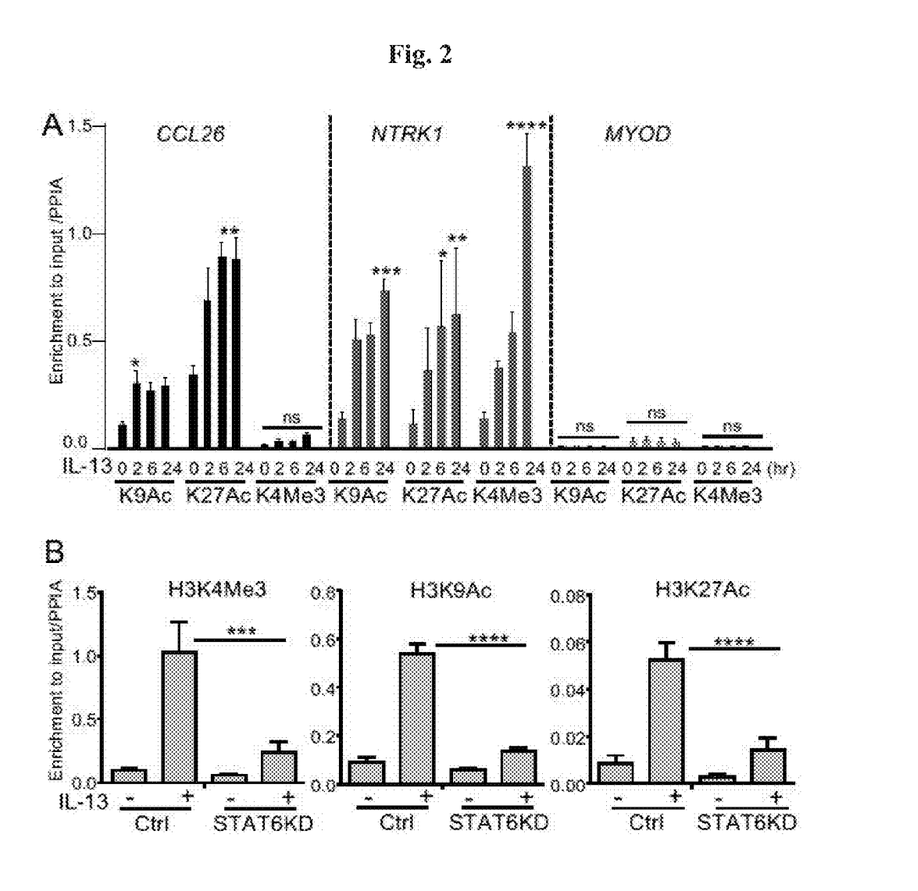

We analyzed the levels of the activating epigenetic marks H3K9Ac, H3K27Ac, and H3K4me3, which reside on actively transcribed genes, in the promoter of NTRK1. Quantitative kinetic analysis revealed the presence of activating chromatin marks prior to IL-13 stimulation and the progressive increase in the levels of H3 acetylation and methylation with IL-13 stimulation, starting from the 2-hr time point (FIG. 2A, NTRK1). Similarly, the promoter of CCL26 (positive control) was marked by histone acetylation, especially H3K27Ac, prior to IL-13 stimulation, and the level of acetylation was significantly increased after IL-13 stimulation; the level of H3K4me3 was not significantly affected by IL-13 (FIG. 2A, CCL26). As a negative control, activating epigenetic marks were absent in the promoter of the myogenic differentiation 1 (MYOD) gene, which was neither expressed nor induced in TE-7 cells (FIG. 2A, MYOD). We next examined the requirement for STAT6 in epigenetic regulation of NTRK1. We utilized TE-7 STAT6 knockdown cells to assess the level of acetylation and methylation chromatin marks in the NTRK1 promoter following IL-13 stimulation. We found that the IL-13-mediated increase in activating chromatin modifications was dependent on STAT6 (FIG. 2B). Collectively, these data identified NTRK1 as a direct early transcriptional and epigenetic target of IL-13 in human epithelial cells.

IL-13-Induced NTRK1 Confers Epithelial Cell Responsiveness to NGF

Figure 3:
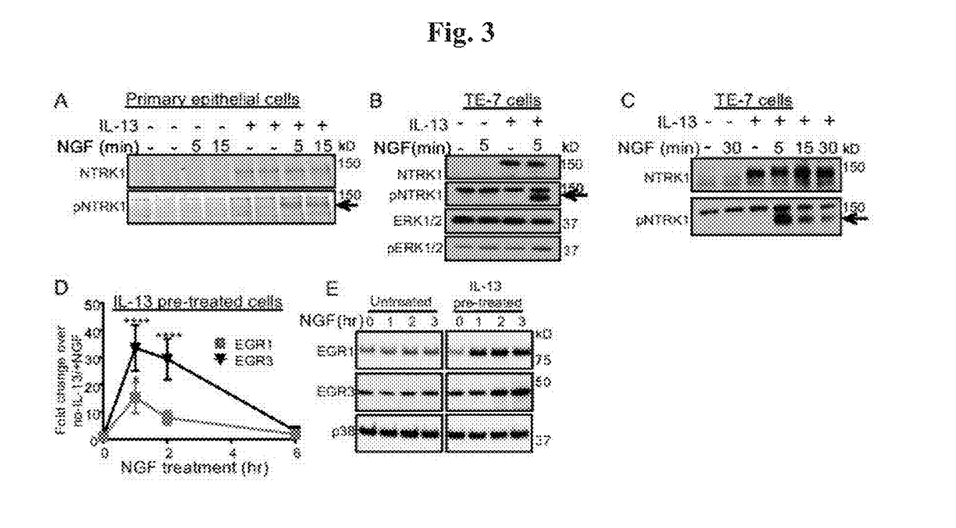

NTRK1 belongs to the family of mitogen-activated protein (MAP) kinase receptors, which undergo dimerization and phosphorylation on tyrosine residues in response to NGF stimulation. Subsequently, downstream signaling events are induced including stimulation of the RAS/RAF pathway, PLC recruitment, and PI3 kinase activation. To assess the functionality of IL-13-induced NTRK1 in epithelial cells, we tested the ability of NGF to induce signal transduction in primary epithelial and TE-7 cells pre-treated with IL-13. Western blot analysis showed that NTRK1 was not detected in resting cells but was induced after IL-13 stimulation in primary esophageal epithelial cells and TE-7 cells (FIG. 3A, B, NTRK1 panel). Subsequent stimulation with NGF caused rapid phosphorylation of tyrosine residues Tyr674/675 in the catalytic domain of NTRK1 (FIG. 3A, B, pNTRK1 panel), as well as increased phosphorylation of ERK1/2 (FIG. 3B, pERK1/2 panel) in IL-13-treated cells. In agreement with previous reports, NTRK1 showed rapid kinetics of Tyr674/675 phosphorylation with peak expression at 5 min and a progressive decrease over 30 min after NGF stimulation (FIG. 3C). To demonstrate that NGF stimulation caused a transcriptional response, we measured the levels of EGR1 and EGR3 mRNA, which are known to be transcriptional targets of NGF in PC12 pheochromocytoma cells. In IL-13-pre-treated cells, but not in untreated cells, we observed a rapid and transient increase in EGR1 and EGR3 transcripts, which peaked at 1 hr after NGF addition (FIG. 3D). Accordingly, increased EGR1 and EGR3 protein levels were detected after NGF stimulation of IL-13-pre-treated cells (FIG. 3E). Taken together, these data show that IL-13 induces functional NTRK1 and thereby confers NGF sensitivity to human epithelial cells.

Figure 4:
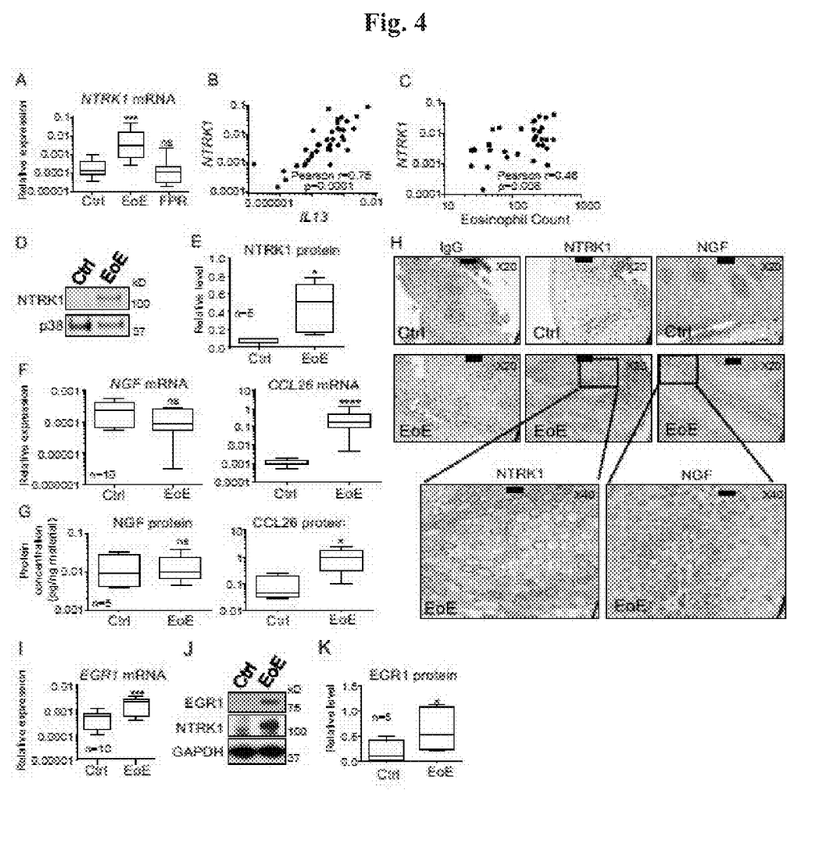

NTRK1 and EGR1, but not NGF, are Increased in Esophageal Biopsies from EoE Patients In vitro experiments with epithelial cells prompted us to investigate whether NTRK1 is increased in epithelial cells in vivo during allergic responses. First, we assessed expression of NTRK1 mRNA in esophageal biopsies of control and EoE patients. RT-PCR analysis showed a highly significant increase of NTRK1 expression in the biopsies of patients with active EoE compared to unaffected control individuals (FIG. 4A, p<0.001). In addition, NTRK1 was dynamically expressed as a function of disease activity, as the esophagus of patients who responded to swallowed steroid treatment (fluticasone propionate responders [FPR]) had normalized levels (FIG. 4A, FPR). Levels of NTRK1 mRNA highly correlated with IL-13 mRNA (FIG. 4B, r=0.75, p=0.0001) and with eosinophil counts in biopsies of EoE patients (FIG. 4C, r=0.46, p=0.006). Accordingly, NTRK1 protein was significantly increased in biopsies from patients with active EoE compared to unaffected individuals (FIG. 4D, E). Notably, neither mRNA nor protein levels of NGF were significantly altered in the biopsies from EoE patients; as a positive control, CCL26 mRNA and protein were highly increased (FIG. 4F, G) Immunohistochemistry of control and EoE biopsies substantiated our findings by showing positive NTRK1 staining in the cytoplasm and membrane of epithelial cells in the basal layer in active EoE samples but not in control unaffected samples (FIG. 4H). Notably, NGF showed diffuse staining throughout the esophageal epithelium independent of the disease activity. Therefore, whereas the ligand NGF is constitutively expressed, NTRK1 is induced by IL-13 and during allergic inflammation. Collectively, these data establish a mechanism wherein the receptor, but not the ligand, is the limiting checkpoint in the pathway. Furthermore, we tested the expression level of EGR1, the main transcriptional target of NGF/NTRK1 signaling 15 in the biopsies of patients with active EoE and found that both the mRNA and protein levels of EGR1 were significantly increased in the biopsies from patients with active EoE compared to control samples (FIG. 4I-K).

Characterization of TE-7 Cells Stably Expressing NTRK1

In order to further investigate the functional link between IL-13 and NGF signaling we generated two pools of TE-7 cells stably expressing NTRK1 that allowed us to simultaneously induce IL-13 and NGF/NTRK1 responses. The majority of the cells expressed NTRK1 in the cytoplasm and membrane at comparable levels between cell lines, efficiently responded to NGF by phosphorylating NTRK1, and transduced intracellular signaling leading to ERK1/2 phosphorylation. Subsequently, rapid and transient induction of EGR1 was observed, indicating that NTRK1 efficiently elicited a transcriptional response. Notably, while IL-13 efficiently induced CCL26 expression in both control and NTRK1-expressing cells, it failed to induce EGR1 and EGR3 transcription in control clones. As expected, NGF stimulation had no effect on control TE-7 cells, suggesting that NTRK1 is necessary for the activation of EGR genes. Indeed, a decrease in the level of expression of NTRK1 in stable pools and prevention of NTRK1 induction by IL-13 in control pools significantly diminished EGR1 and EGR3 activation by NGF.

We further hypothesized that inhibition of NTRK1 kinase activity will prevent induction of EGR genes following NGF stimulation. To test this hypothesis we utilized two tyrosine kinase inhibitors lestaurtinib (CEP-701) and crizotinib that were previously reported as efficient blockers of NTRK1 auto-phosphorylation and downstream signaling. As expected both drugs dramatically reduced the NGF-mediated increase in EGR1 and EGR3 mRNA. These data suggest that functional NTRK1 is required for efficient EGRs stimulation in epithelial cells.

NTRK1 and IL-13 Synergize in Propagating Allergic Responses

Figure 5:
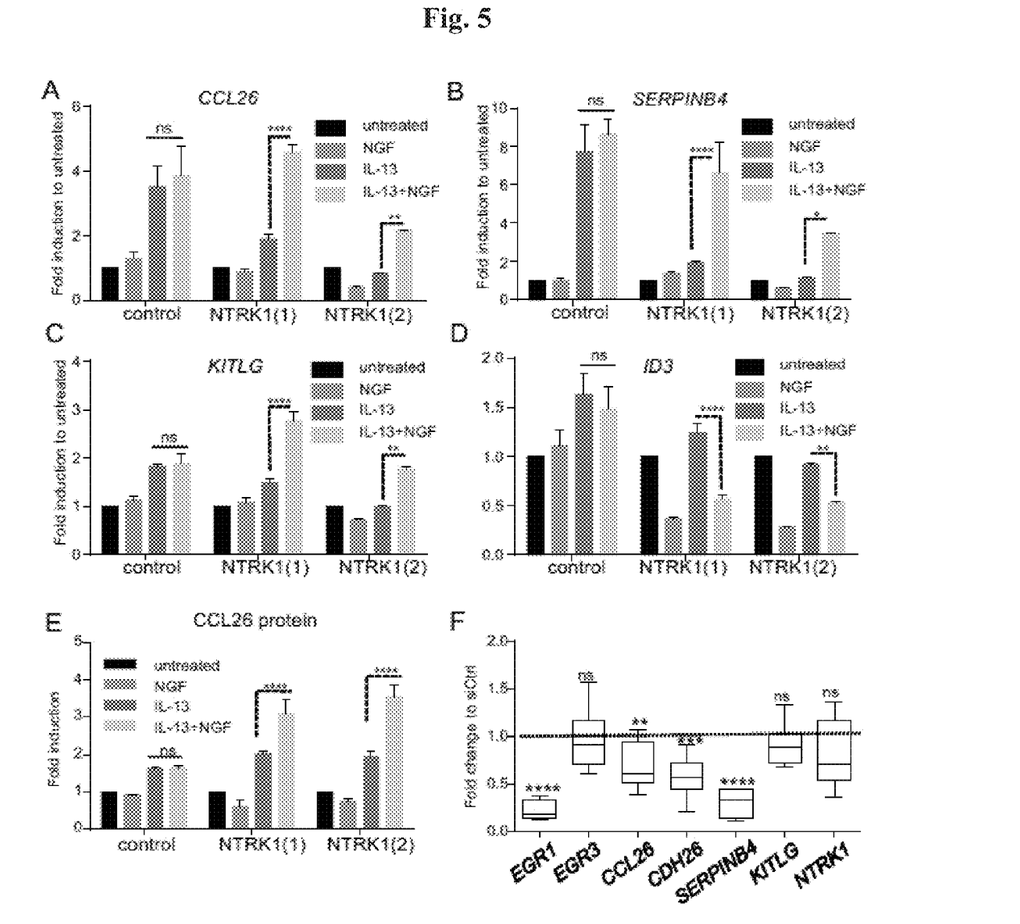

As readout of functional interaction between NGF/NTRK1 and IL-13, we measured transcription of several known IL-13 target genes, including CCL26, the molecular driver of eosinophilic infiltration in EoE. We stimulated TE-7 cells with IL-13 and NGF either alone or in combination for the period of 6 hr and quantified mRNA levels of the genes. Exposure to NGF alone had no effect on the level of CCL26, SERPINB4, KITLG, or ID3 mRNA, whereas induction with IL-13 caused increased expression of these genes. In NTRK1-expressing cells, the transcription of CCL26, SERPINB4, KITLG but not ID3 was synergistically increased by NGF and IL-13 (FIG. 5A-D). In agreement with these data, secretion of CCL26 from NTRK1-expressing cells after co-stimulation with IL-13 and NGF was significantly higher compared with either signal alone (FIG. 8E). Collectively, these findings demonstrated the potential of synergistic interaction between NGF/NTRK1 and IL-13 in propagating allergic inflammation.

EGR1 is Required for Efficient Induction of IL-13 Target Genes

EGR1 has been previously implicated in IL-13-mediated allergic inflammation and tissue remodeling in mice 16. Although we could not detect increased EGR1 expression after IL-13 stimulation, synergistic induction of several IL-13 target genes by IL-13 and NGF prompted us to test whether EGR1 is required for efficient IL-13 response in esophageal epithelial cells. As TE-7 cells express detectable levels of EGR1 at baseline, we utilized an siRNA approach to decrease EGR1 expression in TE-7 cells prior to IL-13 stimulation. We efficiently downregulated EGR1, but not EGR3 expression in cells by about 3 to 5-fold (FIG. 5F, EGR1, EGR3). In TE-7 cells with decreased EGR1 level, the ability of IL-13 to induce expression of some target genes (CCL26, CDH26 and SERPINB4), but not others (KITLG, NTRK1) was significantly diminished (FIG. 5F). These findings implicate EGR1 in the propagation of IL-13-mediated allergic inflammation in human epithelial cells and provide mechanistic insight into synergistic interaction between NGF and IL-13 pathways.

DISCUSSION

By analyzing the kinetics of gene expression in IL-13-stimulated human epithelial cells, we have identified NTRK1, a high-affinity receptor for NGF, as a direct transcriptional and epigenetic target of IL-13. In support of this finding, we showed that NTRK1 was highly induced by IL-13 in epithelial cells, including those derived from several sources (e.g. bronchi and esophagus). This induction was STAT6 dependent and readily detectable as early as 2 hr after IL-13 addition, and the level of NTRK1 decreased as IL-13 was withdrawn (data not shown). In addition, in response to IL-13, the NTRK1 promoter acquired a set of activating epigenetic marks including histone H3 acetylation and trimethylation as early as 2 hr after IL-13 addition and continued accumulating these marks throughout the stimulation in a STAT6-dependent manner, mirroring the expression pattern of the gene.

Translational studies showed elevated NTRK1 expression in the biopsies of patients with active EoE and that this increased NTRK1 expression normalized after steroid treatment. Moreover, NTRK1 mRNA levels strongly correlated with the markers of disease activity, such as IL-13 mRNA level and eosinophil counts. This pattern of expression resembles that of CCL26, a critical eosinophil chemo attractant in the pathogenesis of EoE. Our in vitro finding that NGF and IL-13 synergistically induce a number of hallmark genes including CCL26 in conjunction with in vivo data showing dynamic expression of NTRK1 as a function of disease severity collectively suggest that the NGF/NTRK1 and IL-13/STAT6 pathways functionally cooperate in propagating allergic inflammation. We indeed observed increased levels of EGR1, a central transcriptional target of NGF, in biopsies of patients with active EoE. EGR1 has been previously shown to be induced in lung epithelial cells exposed to dust mite allergen and to play an important role in the induction of Th2-related chemokines. EGR1 is rapidly and transiently induced in response to various stimuli, including growth factors or cytokines mechanical stress, and hypoxia. Therefore, we cannot definitively state that EGR1 elevation is solely due to NGF/NTRK1 signaling. Regardless, these findings suggest potential functional interactions of NGF/NTRK1 and IL-pathways in the pathogenesis of allergic inflammation.

Unlike mouse models, we could not detect increased level of EGR1 in response to IL-13 stimulation. Yet our findings that decreased EGR1 expression correlated with diminished IL-13 response suggest that EGR1 synergizes with IL-13 in induction of early target genes presumably by interacting with STAT6. Cooperative interaction of EGR1 with other transcription factors, such as nuclear factor of activated T-cells (NFAT) and nuclear factor kappa-B (NFkB) has been previously reported in T cells. Similarly, synergistic interaction between STAT6 and NFkB in IL-4-induced transcription has been shown. Moreover, EGR1 has been implicated in the formation of chromatin loops required for its synergistic interaction with other transcriptional factors, substantiating the potential role of epigenetics in allergic transcriptional response. Notably, EGR1 was required for efficient IL-13 induction of some but not all genes, suggesting that other factors are required for synergistic activation of target genes by IL-13 and NGF during propagation of allergic inflammation.

Epigenetics is considered as a possible mechanism involved in the development of many disorders, including allergic diseases. The most common epigenetic mechanisms include DNA methylation, histone modifications, and non-coding RNAs, all of which can affect gene transcription through effects on DNA structure and inducing gene silencing. We have previously demonstrated that these mechanisms are involved in IL-13-mediated allergic inflammation. Accordingly, IL-13-mediated NTRK1 induction was accompanied by increased levels of activating epigenetic modifications. Notably, we have found high levels of activating marks in the promoter of NTRK1 prior to IL-13 stimulation, suggesting that NTRK1 is epigenetically poised for induction. Similarly, elevated levels of histone acetylation were observed in the CCL26 promoter, collectively suggesting that epigenetic poising may be a common mechanism of induction for early IL-13 targets. Interestingly, the level of the H3K4me3 mark, which is commonly present at the promoters of transcribed genes, was relatively low on the CCL26 promoter compared to NTRK1. A low level of H3K4me3 has been observed previously in ~20% of expressed genes and the percentage of genes with the H3K4me3 mark was not increased following cell activation. The low level of H3K4me3 in the promoter of the CCL26 gene may reflect a more "enhancer like" signature of this region, which is consistent with the known signature of active enhancers (low H3K4me3, high H3K27Ac). Alternatively, it is possible that the peak of H3K4me3 in the promoter of CCL26 is shifted relatively to other histone marks and therefore is not detected by RT-PCR. Performing ChIP-sequencing experiments should differentiate between these possibilities. The ultimate goal of future studies will be the comprehensive characterization of the IL-13-mediated epigenome by ChIP-sequencing and utilizing this knowledge in developing new diagnostic and therapeutic strategies in allergy.

Figure 6:
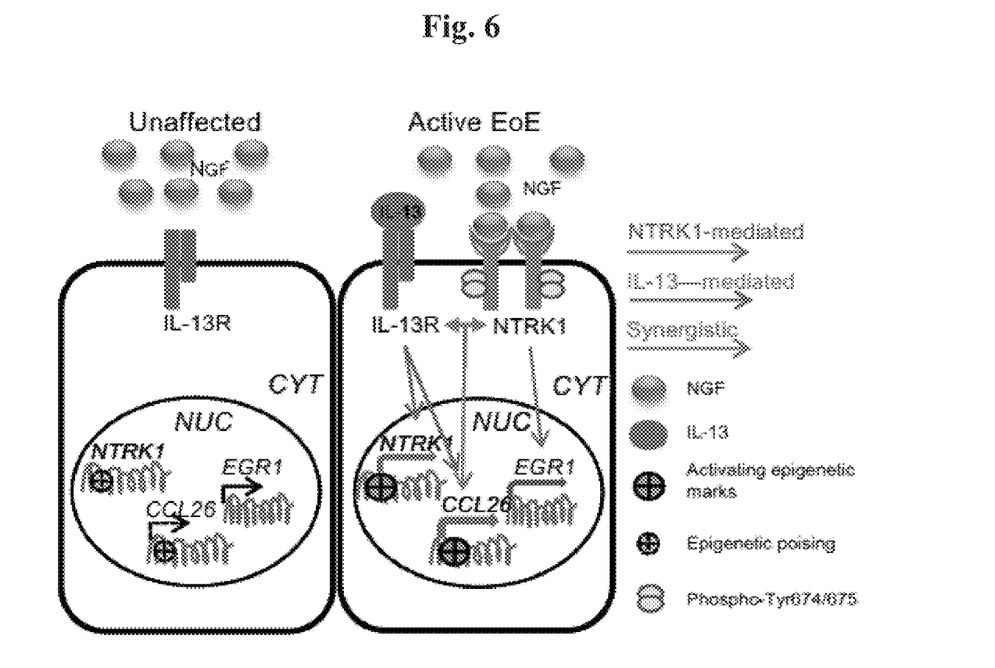

Among the 90 RTKs identified in the human genome, NTRK1 was the only one induced both transcriptionally and epigenetically by IL-13 in esophageal epithelial cells. Remarkably, we did not observe significant changes in the NGF level in esophageal biopsies, where it was detected independent of disease status. Transcriptional regulation of NTRKs has been widely investigated; however, to the best of our knowledge, these data are the first example of regulating NTRK1 signaling by modulating the level of the receptor rather than the ligand in human epithelial cells. One previous study described down regulation of NTRK1, but not NGF, in the cerebellum of rat pups exposed to ethanol. On the basis of our findings, we propose an NTRK1/IL-13 axis is involved in the propagation of allergic inflammation (FIG. 6). In this model, early transcriptional targets of IL-13 in epithelial cells are epigenetically poised for expression, as evident from the presence of activating epigenetic marks on the promoters of genes prior to IL-13 stimulation. IL-13 causes increased expression of NTRK1 together with other early transcriptional targets (CCL26) accompanied by augmenting epigenetic changes in the promoters of these genes. Subsequently NTRK1 becomes activated by the extracellular pool of NGF molecules, which in turn leads to NTRK1-mediated transcriptional responses (e.g. increased EGR1), as well as synergistic interaction with IL-13 in eliciting transcription and secretion of CCL26 and other mediators of the allergic response.

In summary, we identify NTRK1 as an early epigenetic and transcriptional target of IL-13 in human epithelial cells. We provide evidence that NTRK1, but not its ligand NGF, is dramatically up regulated in the biopsies of patients with active EoE, establishing a mechanism wherein the receptor, but not the ligand, is the limiting checkpoint in the pathway. We demonstrate synergistic induction of the critical allergic mediator CCL26 by IL-13 and NGF/NTRK1 signaling, supporting the role of NTRK1 in the pathogenesis of mucosal allergic inflammation.

Our finding that NTRK1 is highly increased in human esophageal biopsies from EoE patients and synergizes with IL-13 in propagating allergic inflammation provides the rationale for pharmacological targeting of NTRK1 signaling. The increasingly recognized link between NTRK1 signaling and cancer progression as well as the critical role of NTRK1 in pain sensitivity has stimulated development of highly specific NTRK1 inhibitors, such as AR-786, AR-256 and AR-618 68. Additionally, the wide range of existing tyrosine kinase inhibitors specific to a number of protein kinases including NTRK1, such as lestaurtinib (CEP-701) and crizotinib, used in our study can be utilized to block NTRK1 activity. Some of these inhibitors have been approved for use in human subjects primarily for cancer treatment Importantly, because NTRK1 is the only protein tyrosine kinase dramatically induced by IL-13 in epithelial cells, even the use of tyrosine kinase inhibitors not specifically developed for NTRK1 may be beneficial for decreasing allergic inflammation. Our experiments provide initial support for the feasibility of this approach.

What is claimed is:

1. A method of treating eosinophilic esophagitis (EoE) in a human subject in need thereof, comprising administering to the subject an amount of a tyrosine kinase inhibitor effective to suppress NTRK1 activity in target cells of the human subject, wherein the tyrosine kinase inhibitor is lestaurtinib (CEP-701) or crizotinib.

2. The method of claim 1, wherein the target cells are epithelial cells.

3. The method of claim 1, wherein the target cells are cells of a target tissue in the subject.

4. The method of claim 1, wherein the target tissue is tracheal, lung, or esophageal tissue.

5. The method of claim 1, wherein the tyrosine kinase inhibitor is effective to suppress NTRK1 activity in the cells of the subject, relative to untreated cells.

6. The method of claim 5, wherein the tyrosine kinase inhibitor is effective to suppress NTRK1 gene expression or protein expression, or both.

7. The method of claim 1, wherein the amount of the tyrosine kinase inhibitor is effective to ameliorate one or more symptoms of the EoE.

8. The method of claim 1, further comprising administering to the subject at least one additional active agent.

9. The method of claim 8, wherein the at least one additional active agent is an anti-inflammatory agent.

10. The method of claim 8, wherein the at least one additional active agent is an IL-13 inhibitor, a non-steroidal anti-inflammatory drug (NSAID), a cytokine inhibitor, or a steroid.

\* \* \* \* \*